United States Patent
Stark et al.

(10) Patent No.: US 6,540,707 B1
(45) Date of Patent: *Apr. 1, 2003

(54) ORTHOSES

(75) Inventors: John G. Stark, Deephaven, MN (US); Duane P. Oyen, Maple Grove, MN (US)

(73) Assignee: IZEX Technologies, Inc., Golden Valley, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/824,065

(22) Filed: Mar. 24, 1997

(51) Int. Cl.[7] .................................................. A61F 5/01
(52) U.S. Cl. ............................ 602/13; 602/19; 600/594
(58) Field of Search ..................... 602/13, 19; 601/148, 601/151; 600/594; 128/118.1, DIG. 20

(56) References Cited

U.S. PATENT DOCUMENTS

| | | | |
|---|---|---|---|
| 3,521,623 A | * 7/1970 | Nichols et al. | ............... 602/13 |
| 3,667,457 A | * 6/1972 | Zumaglini | ................... 602/19 |
| 3,734,087 A | 5/1973 | Sauer et al. | |
| 3,866,604 A | 2/1975 | Curless et al. | |
| 4,039,039 A | 8/1977 | Gottfried | |

(List continued on next page.)

FOREIGN PATENT DOCUMENTS

| | | | | |
|---|---|---|---|---|
| NL | 7806327 | * | 12/1979 | .................. 602/13 |
| SU | 1380747 | * | 3/1988 | .................. 602/19 |
| SU | 1750681 | * | 7/1992 | .................. 602/19 |

OTHER PUBLICATIONS

Biering–Sorensen, A One–Year Prospective Study of Low Back Trouble in a General Population, *Danish Medical Bulletin*, vol. 31, No. 5, pp. 362–375 (Oct. 1984).
During et al., "Toward Standards for posture—Postural Characteristics of the Lower Back System in Normal and Pathologic Conditions", *Spine*, vol. 10, No. 1, pp. 83–87 (1985).
Kishino et al., "Quantification of Lumbar Function—Part 4: Isometric and Isokinetic Lifting Simulation in Normal Subjects and Low–Back Dysfunction Patients", *Spine*, vol. 10, No. 10, pp. 921–927 (1985).
Elnaggar et al., "Effects of Spinal Flexion and Extension Exercises on Low–Back Pain and Spinal Mobility in Chronic Mechanical Low–Back Pain Patients", *Spine*, vol. 16, No. 8, pp. 967–972 (1991).
Mayer et al., "Quantification of Lumbar Function—Part 2: Sagittal Plane Trunk Strength in Chronic Low–Back Pain Patients", *Spine*, vol. 10, No. 8, pp. 765–772 (1985).

(List continued on next page.)

*Primary Examiner*—Jerome W. Donnelly
*Assistant Examiner*—Victor K. Hwang
(74) *Attorney, Agent, or Firm*—Patterson, Thuente, Skaar & Christensen, P.A.; Peter S. Dardi

(57) ABSTRACT

Exercise orthoses are described that include a frame, a fluid bladder held by the frame, a pressure sensor attached to the fluid bladder and a microprocessor receiving the pressure measurements. The microprocessor monitors variations in pressure and determines differences between the measured pressures and predetermined target values. The frame can be designed to support a hinge joint or at least one vertebra. Furthermore, corrective back orthoses are described that include a frame, force applicators connected to the frame to apply force to the patient's spine, a sensor that measures forces associated with the force applicators and a control unit that monitors forces measured by the sensor. The corrective back orthosis can include fluid bladders as force applicators. The control unit can include a microprocessor.

18 Claims, 3 Drawing Sheets

U.S. PATENT DOCUMENTS

| | | | |
|---|---|---|---|
| 4,135,503 A | * | 1/1979 | Romano ............... 602/13 |
| 4,178,923 A | * | 12/1979 | Curlee ............... 602/13 |
| 4,256,094 A | | 3/1981 | Kapp et al. |
| 4,270,527 A | | 6/1981 | Peters et al. |
| 4,331,133 A | | 5/1982 | Arkans |
| 4,375,217 A | | 3/1983 | Arkans |
| 4,396,010 A | | 8/1983 | Arkans |
| 4,408,599 A | | 10/1983 | Mummert |
| 4,419,988 A | | 12/1983 | Mummert |
| 4,553,124 A | | 11/1985 | Malicki |
| 4,590,925 A | | 5/1986 | Dillon |
| 4,604,098 A | | 8/1986 | Seamone et al. |
| 4,697,808 A | | 10/1987 | Larson et al. |
| 4,757,453 A | | 7/1988 | Nasiff |
| 4,762,134 A | * | 8/1988 | Gala ............... 600/594 |
| 4,858,620 A | | 8/1989 | Sugarman et al. |
| 4,913,163 A | | 4/1990 | Roger et al. |
| 4,928,674 A | * | 5/1990 | Halperin et al. ........... 601/44 |
| 5,031,604 A | | 7/1991 | Dye |
| 5,050,618 A | | 9/1991 | Larsen |
| 5,116,296 A | | 5/1992 | Watkins et al. |
| 5,121,747 A | | 6/1992 | Andrews |
| 5,186,163 A | | 2/1993 | Dye |
| 5,218,954 A | | 6/1993 | van Bemmelen |
| 5,307,791 A | * | 5/1994 | Senoue et al. ....... 128/DIG. 20 |
| 5,360,392 A | * | 11/1994 | McCoy ............... 602/19 |
| 5,391,141 A | | 2/1995 | Hamilton |
| 5,396,896 A | | 3/1995 | Tumey et al. |
| 5,437,610 A | | 8/1995 | Cariapa et al. |
| 5,437,617 A | * | 8/1995 | Heinz et al. ............... 602/19 |
| 5,443,440 A | | 8/1995 | Tumey et al. |
| 5,462,504 A | | 10/1995 | Trulaske et al. |
| 5,484,389 A | * | 1/1996 | Stark et al. ............... 601/34 |
| 5,520,622 A | * | 5/1996 | Bastyr et al. ............... 602/13 |
| 5,558,627 A | | 9/1996 | Singer et al. |
| 5,586,067 A | * | 12/1996 | Gross et al. ............... 702/139 |
| 5,713,841 A | * | 2/1998 | Graham ............... 128/DIG. 20 |
| 5,827,209 A | * | 10/1998 | Gross ............... 602/19 |

OTHER PUBLICATIONS

Million et al., "Assessment of the Progress of the Back–Pain Patient", *Spine*, vol. 7, No. 3, pp. 204–212 (1982).

*Rehabilitation of the Spine—Science and Practice*, Pollock et al., "*Muscle*", Chapter 22, pp. 263–284.

Sikorski, "A Rationalized Approach to Physiotherapy for Low–Back Pain", *Spine*, vol. 10, No. 6, pp. 571–579 (1985).

Smidt et al., "Assessment of Abdominal and Back Extensor Function—A Quantitative Approach and Results for Chronic Low–Back Patients", *Spine*, vol. 8, No. 2, pp. 211–219 (1983).

*Air Back*™ *Spinal System* Product Literature, four pages, 1993.

Clinical Biomechanics of the Spine, 2nd Edition, p. 482, 1990.

* cited by examiner

ORTHOSES

FIELD OF THE INVENTION

The invention relates to orthotic devices and associated methods that assist with healing or correction of musculoskeletal defects or injuries.

BACKGROUND OF THE INVENTION

The musculoskeletal system involves a network of ligaments, cartilage, muscle, bone and the like, which are generally controlled by the nervous system. The musculoskeletal system is subject to a variety of stresses, trauma and congenital defects. Surgery may be required to address certain problems, and physical therapy may solve other problems. In addition, a physician can use a variety of orthotic devices such as braces to stabilize an injured or diseased body part. The orthotic device may form an integral component of the treatment process.

The treatment process can involve a variety of stages that will strongly depend on the specific problem involved and on access to effective treatment methods. Exercise is a part of many treatment programs. It is known that properly designed exercise can increase the speed and improve the quality of the healing of many musculoskeletal injuries. But it is also recognized that inappropriate exercise can cause additional injury or slow healing.

Relatively sophisticated braces with built in transducers can be used to monitor an exercise program. The transducers measure the forces being exerted during an exercise routine. These braces serve a variety of purposes. An important purpose is to assist patients in monitoring their exercise while minimizing the risk of additional injury. Furthermore, these braces can assist the responsible physician to monitor efficiently the progress of the patient and to adjust the exercise program according to the progress or lack of progress by the patient.

Back problems are examples of musculoskeletal injury and are ubiquitous in our society. The spine has 24 motion segments. Forces and injury are concentrated at areas of transition between the spine's most rigid and most flexible segments. This results in a tendency towards degenerative problems at the lower levels of the flexible elements of the lumbar and cervical spine. The spine involves an interrelationship of static soft tissue (e.g., ligaments and cartilage), muscle, flexible connective tissue (e.g., facet joints and disc spaces), bone, and nerve elements (including spinal cord, autonomic and radicular structure). This complex structure creates an enormously complex problem for the clinician attempting to assist a patient through a period of symptomatology.

Exercise is important for achieving and maintaining a healthy spine. Studies suggest that back muscles maintain the erect posture of the spine throughout the day. This requires a certain level of back muscle strength and endurance. This endurance is also necessary for lifting and load carrying. Therefore, specific and properly controlled exercises for back muscle strength and endurance may be useful in preventing or improving some lower back trouble.

In addition to problems of degeneration and weakness, misalignment of the spine can result in a variety of problems and can result in progressive degeneration. For example, adolescent idiopathic scoliosis affects approximately 1 to 3 percent of the juvenile population. The deformity appears during early adolescence as lateral curvature of the spine in either single curve or double curve patterns.

The most frequent locations of scoliosis are in the thoracic (chest area) and lumber (lower back region). A common pattern is the double "thoracolumbar curve" in which the spine resembles an "S" as the spine curves first one way in the chest area, then back the other way in the lower back. As the spine curves, it also rotates, producing either thoracic or lumbar prominences. Adolescent idiopathic scoliosis is a progressive disease, which often grows worse with the passage of time. The progression rate is significantly higher in young girls than in boys. Bracing can be successful in reducing or arresting progression.

Besides producing an undesirable appearance, spinal curvature can result in nerve compression as a result of impingement on nerve roots passing out from the spine to the limbs. In addition, spinal curvature can also result in reduced thoracic capacity including reduced cardiac and pulmonary function. These difficulties result from the size and shape of the chest. In extreme cases, premature death follows a lifetime of discomfort and deformity.

In certain circumstances, direct intervention to correct the curvature of the spine is indicated. Ultimately, about one youth in one thousand out of the general population is treated with bracing. Back braces, such as the Jewett brace, can be used to apply corrective forces to the spine.

The commitment to place an adolescent in a restricting device that encompasses the main trunk for long periods of time is a serious one due to the physical discomfort factors and the direct expense of fitting the brace and monitoring the disease through the treatment period. In spite of these deterrents, bracing is the most frequent treatment for adolescent idiopathic scoliosis because of the seriousness of the disease.

Surgery to fuse vertebrae in better positions is an alternative to bracing. Often in this surgery, rods are inserted along the side of the spine and tied to the vertebrae to hold the vertebrae in a better position. This surgery is a major and costly procedure and typically leads to lessened flexibility. Therefore, every effort is made to minimize the impact of the pathology and to avoid surgery, if possible. Alternatives to surgery include bracing for passive correction of the spinal deformity, and exercise for improved strength and control. Managed care providers often require bracing before surgery is attempted to correct or to stabilize spinal curvature.

SUMMARY OF THE INVENTION

The present invention involves a portable orthopedic restraining device for the passive correction of biological deformity and/or the exercising of muscles and other tissues associated with a joint or joints of a patient. In preferred embodiments the orthopedic restraining device includes bladders with pressure sensors. The bladders absorb some of the forces, and fluctuations in the bladder pressure provide for measurements of the forces applied by the patient. Bladders spread the forces over the patient's skin and provide a direct measure of the forces on the skin to provide a warning if the pressures reach a level that would cause injury to the skin.

The invention includes corrective back orthoses. The corrective back orthoses provide for monitoring of the forces applied by the orthoses to permit more optimal use of the orthoses. In certain embodiments, bladders are used advantageously in the force applicators. The corrective back orthoses can include microprocessors for more sophisticated monitoring of compliance, variations in applied force and estimates of changes in the patient's condition.

Specifically, in a first aspect, the invention involves an orthopedic restraining device including:

(a) a frame, which can restrain a first flexibly connected body portion of an individual relative to a second flexibly connected body portion;

(b) at least one bladder held by the frame, where the bladder contacts at least one of the flexibly connected body portions when the frame is restraining the flexibly connected body portions;

(c) a pressure sensor attached to the bladder such that pressure within the bladder is measured; and (d) a microprocessor receiving the pressure measurements, where the microprocessor monitors variations in pressure and determines differences between the measured pressures and predetermined target values.

The frame can include a hinge or an articulating section. The bladder preferably is positionable relative to the frame to adjust the rest pressure within the bladder. The bladder preferably holds air. The first flexibly connected body portion of the individual and the second flexibly connected body portion can be connected by many types of joints such as hinge, ball and socket, intervertebral disc or synchondrosis. The orthopedic restraining device can further include a display for displaying a quantity related to the pressure.

In another aspect, the invention involves a corrective back orthosis including:

(a) a frame that fits around at least a portion of a patient's torso to surround a portion of the patient's spine;

(b) a bladder supported by the frame, where the bladder is positioned to provide corrective forces to the spine of the patient; and (c) at least one pressure sensor attached to the bladder such that pressure within the bladder is measured.

The corrective back orthosis can further include a microprocessor, which monitors pressures measured by the sensor. The corrective back orthosis also can further include a graphic display interfaced to the microprocessor, where the graphic display depicts the forces along spinal orientations of the patient in order to permit adjustment of the forces through changes in pressure in the bladder. In addition, the corrective back orthosis can include a valve providing for the release of fluid from the bladder. The corrective back orthosis can include a plurality of bladders.

The corrective back orthosis preferably further includes a manual pump attached to the bladder such that activation of the manual pump adjusts pressure in the bladder by varying the amount of fluid within the bladder. The valve can be controlled by a microprocessor. The corrective forces applied by the corrective back orthosis preferably are oriented along a plurality of vectors. The corrective back orthosis can include a plurality of bladders with independently adjustable pressures.

In another aspect, the invention involves a corrective back orthosis including:

(a) a frame that fits around at least a portion of a patient's torso to surround a portion of the patient's spine;

(b) force applicators connected to the frame to apply force to the patient's spine;

(c) a sensor that measures forces associated with the force applicators; and (d) a control unit connected to the force sensor for displaying values related to the measured forces.

The control unit can include a microprocessor that monitors forces measured by the sensor. The corrective back orthosis can further include a graphic display interfaced to the microprocessor, where the graphic display depicts the forces along spinal orientations of the patient in order to permit adjustment of the forces. The corrective back orthosis also can further include strain gauges operably connected to the frame.

In another aspect, the invention involves a method of correcting spinal misalignment of a patient including the step of applying appropriate corrective forces to the spine using a back orthosis comprising at least one bladder and a pressure sensor positioned to measure pressure associated with the bladder, where the bladder is positioned to provide a contribution to the corrective forces and is adjusted to a desired inflation. The appropriate corrective forces preferably are oriented along a plurality of vectors. The back orthosis used in practicing the method can further include a microprocessor, which monitors pressures measured by the sensor and determines variation in the measured pressure and predetermined desired values. The microprocessor preferably is interfaced to a graphic display to provide a graphic analysis of the spinal deterioration and the vectors of the corrective forces used to correct the deterioration. The microprocessor can control a release valve to adjust pressure within the bladder. The method can further include the step of estimating using the microprocessor evolving force vectors based on estimated evolving conditions of the patient.

In another aspect the invention involves a method of correcting spinal misalignment including the step of applying appropriate corrective forces to the spine using a back orthosis comprising: a) force applicators connected to a frame that fits around at least a portion of a patient's torso to surround a portion of the patient's spine, b) a sensor that measures forces associated with the force applicators and c) a control unit that displays values related to the measured forces.

DESCRIPTION OF THE PREFERRED EMBODIMENTS

Figure 1:
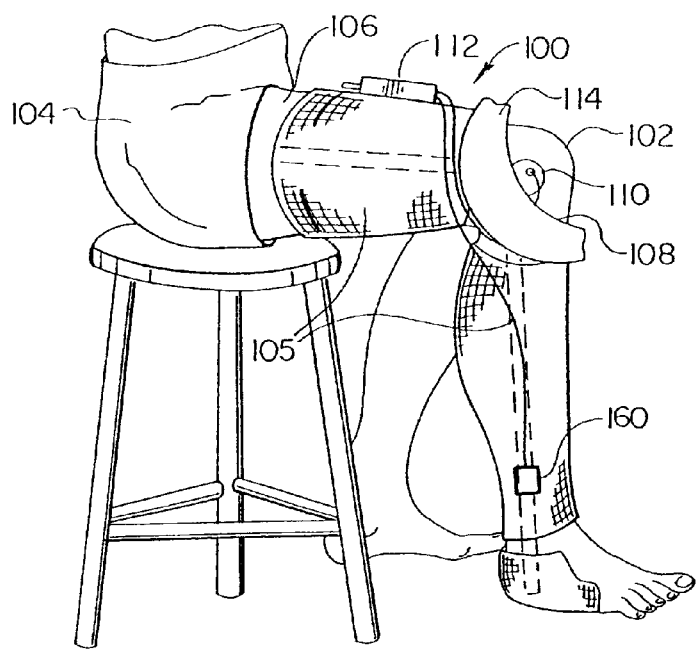
FIG. 1 is a perspective view of an exercise orthosis of the invention on the leg of a patient, where the orthosis involves a bladder.

The present invention involves the incorporation of innovative technology to a variety of orthopedic braces. In a first type of orthosis, an improved orthopedic restraining device, such as a brace, involves the incorporation of a bladder into a device that supports two flexibly connected body portions. Such a bladder preferably is filled with a fluid, e.g., a liquid or gas. This device is designed for exercise of the portion of the patient's body within the device. The pressure within the bladder is monitored for a variety of purposes.

In addition, a back orthotic applies corrective forces to a patient's spine to assist with correcting improper curvature. The orthotic includes force applicators for applying the corrective forces. The force applicators can be bladders, which can be filled with a liquid or gas. In any case, sensors are included for measuring the corrective forces. In preferred embodiments, a microprocessor monitors the application of the corrective forces to provide the responsible physician with valuable information.

Exercise Orthosis

Bracing is used to support and align in many areas of orthopaedics. The fundamental principles of bracing include mechanical alignment, removal of abnormal stresses by providing support, as with a splint or cast, and restoration of normal physiology. While bracing is fundamental, it has limitations even when involving a hinge joint such as the knee or elbow. The limitations involve the fit of the orthosis to the soft tissue, contact interface, e.g. skin care, and translation of the device through physiologic or more limited range of motion.

With respect to the present exercise orthosis, the bladder provides for cushioning of the forces within the brace generated by the patient's exercising. Also, the bladder may spread the forces over a significant surface area of the skin. The spreading of the forces may vary according to the amount of fluid within the bladder. Nevertheless, the forces on the skin can be sufficient to injure the patient due to damage of or interference with neural or circulatory functions. Measuring the pressure is a direct way to determine if excessive forces are being applied to the patient's skin.

In addition, the pressure is a measure of the forces being exerted by the patient. In this way, the exercise can be monitored to determine if the patient is following a predetermined exercise routine. Orthoses for supporting a portion of the body and for exercise, especially isometric exercise, have used strain gauges within the structure of the device to measure the forces applied during exercise. See, U.S. Pat. No. 5,052,375, incorporated herein by reference. While the pressure in the bladder may not provide directly the forces applied by the exercising patient, the pressure can be used to monitor the exercise routine in a meaningful way if the bladder is positioned and inflated properly.

Generally, the exercise orthosis will contain one or more bladders attached to a frame. The frame can take any form that provides a relatively rigid support. For example, the frame can include molded polymer portions that fit around a body portion, or metal supports that connect around a body portion using straps.

The positioning of the bladder will depend on the design of the orthosis and the part of the body to be supported by the orthosis. The bladder should be placed around the joint to be exercised, such that the bladder, when inflated, will contact either the muscle or connective tissue surrounding the joint. In this way, the bladder or bladders can absorb one or more of the significant forces applied by the patient against the brace.

Absorption of these forces by the bladder will result in a change in the pressure in the bladder. The pressure in the bladder is monitored to measure this change. An empirical determination can be made by correlating the variation in pressure measurements with corresponding forces applied by the patient. Such empirical determinations are evaluated for a particular brace design and bladder inflation. Then, an appropriate exercise routine can be designed based on desired pressure changes. The exercise routine can be reevaluated as treatment progresses.

The preferred fluid for placement in the bladder is air, since air can be pumped easily into the bladder and released. A variety of other fluids can be used such as inert gases and liquids. Furthermore, a deformable gelatinous material can be used in the bladder as long as a reasonable pressure can be measured with the material. Also, materials can be used that change phase such as liquids that form a gel once inside the bladder.

Preferably, the amount of fluid in the bladder is variable for adjustment of the bladder within the orthosis. The apparatus used to change the fluid amounts generally will depend on the fluid. Unless air is used, a supply of the fluid will be needed. The valves can be manually adjustable, or they can be controlled electronically through a controller. A valve can be used for filling the bladder, and a separate valve can be used for emptying the bladder, although a single valve can be used. Unless the fluid source is at high pressure, a pump will be needed to pump the fluid into the bladder. An electrical pump can be used, but a manual pump is preferred for cost considerations and for ease of use.

The bladder can be used in a sealed form such that the amount of material within the bladder remains constant. Having a constant amount of material within the bladder may not be optimal since the orthosis generally can be reconfigured for different orientations of the joint. The brace then would have to be adjustable to accommodate the bladder with a constant amount of material in the different positions. Whether the amount of fluid within the bladder is variable or not, it may be desirable to have adjustments, such as straps or hook and loop fasteners, to permit repositioning of the bladders and/or to alter the resting pressure on the bladder.

Referring to FIG. 1, an exercise brace 100 is depicted supporting the knee 102 of a patient 104 in a frame 105. In this embodiment, the two flexibly connected body portions supported by frame 105 are the thigh 106 and the lower leg 108. Frame 105 can include adjustable hinges 110 to permit variation in the angle of brace 100. The angle typically is fixed at a selected position for performing the exercises, which can be isometric, isotonic or other exercises. Hinge 110 can be an electromechanical hinge or a mechanical hinge. A standard hinge can be replaced by an articulating section of the frame that functions as a hinge. Various alternative structures for the hinge and the frame generally are described in U.S. Pat. No. 5,052,375 and WO 96/36278, incorporated herein by reference.

The brace 100 further includes a controller 112 for monitoring and analyzing performance of exercise routines by the patient 104. Controller 112 generally includes a display, which can involve a series of lights or preferably a digital display. Controller 112 preferably includes a microprocessor.

The microprocessor can be interfaced to provide information to a physician. The interface can be provided by a port for connection to another computer or to a modem. Alternatively, the interface can be accomplished by transmission of electromagnetic radiation such as radio waves to a nearby or more distant base station. In some embodiments, the controller can be reprogrammed remotely to adjust the exercise routine according to the evolving status of the patient's condition.

In a preferred embodiment of controller 112, a microprocessor based system has several subsystems. Preferred subsystems include: power supply such as a 9 volt battery, transducer bias circuit, transducer signal conditioning circuit, analog to digital converters, a microprocessor such as a Motorola 68HC11, real time clock, RAM and non-volatile storage such as SRAM or EEPROM, graphic display such as a 64×128 pixel LCD display with corresponding driver, keypad, audible or tactile feedback device, data link to transducer, and RS232 standard output for serial connection or modem access. The total device can be integrated into a single package or physically partitioned between portions mounted directly on frame 105 and portions mounted in a small case, which optionally can be attached to frame 105.

A preferred controller 112 stores a software program that manages the use of the device for patient rehabilitation. The software preferably provides for alerting the patient when exercises are to be done using audible or vibrator signals. The controller 112 under software control preferably provides instructions on the exercises as well as feedback and reinforcement messages to the patient.

A preferred controller 112 counts and tracks exercises in both content and quality, stores the results in non-volatile memory, and puts itself to sleep when inactive to conserve power. The software program can wake up between exercise sessions to confirm periodically the continued use of the orthopedic restraining device 100 and to monitor the forces during a non-exercise mode. The controller 112 preferably accepts software program changes by way of an RS232 serial cable direct computer link or via a telephone modem.

Brace 100 preferably includes a bladder 114, which can be configured in a variety of ways based on the criteria described above. In FIG. 1 the bladder 114 is approximately toroidal in shape. The toroidal bladder 114 is placed with its center positioned roughly over the knee 102. The toroidal bladder 114 can be attached to the brace 100 in a variety of ways including reversible attachment with straps having hook and loop fasteners and permanent attachment by fastening sewing cuffs around another portion of the brace 100.

Bladder 114 can be made from a variety of materials. The material should be puncture resistant and comfortable against the patient's skin. Preferred materials for bladder 114 include, for example, natural rubber, synthetic rubber, thermo plastic elastomers and combinations thereof.

Figure 2:
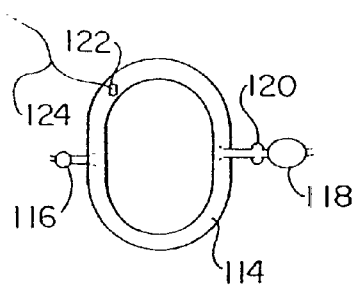
FIG. 2 is a top view of the bladder of FIG. 1 removed from the orthosis.

FIG. 2 displays toroidal bladder 114 separately from the rest of brace 100. Toroidal bladder 114 has an outlet valve 116 and a removable manual inflator 118 attached to the bladder 114 by way of a one way valve 120. A variety of designs can be used for the manual inflator 118. The outlet valve 116 is actuated by squeezing the valve. The manual inflator 118 can be replaced with a variety of motorized pumps, where the pumps are optionally operated by controller 112. Similarly, the outlet valve can be replaced by an electrically controlled valve. Alternatively, a single valve can be used for inflation and deflation. Any of a variety of commercially available valves can be used.

The bladder 114 preferably includes a pressure sensor 122 connected using wire 124 to controller 112. The pressure sensor 122 can be any reasonable type. A variety of suitable pressure sensors are commercially available. Preferred pressure sensors include the MPX series of pressure sensors manufactured by Motorola because of their linear output and small size. Other suitable pressure sensors use silver oxide ink surfaces separated by a dielectric material. If excessive pressures are measured, an alarm can be designed to warn the user in order to avoid skin damage. Furthermore, the pressure readings can be used to monitor the exercise routine, as described further below.

Alternative embodiments of the bladders can be used. Also, a plurality of bladders can be used. These bladders may or may not be positioned in the immediate vicinity of the joint to be exercised since forces will be exerted against contact points within the orthosis away from the joint. Some bladders may only serve to cushion the brace while others are designed for monitoring the exercise routine. Some or all of the bladders will be equipped with a pressure sensor, and some or all of the bladders may be monitored by the controller.

Figure 3:
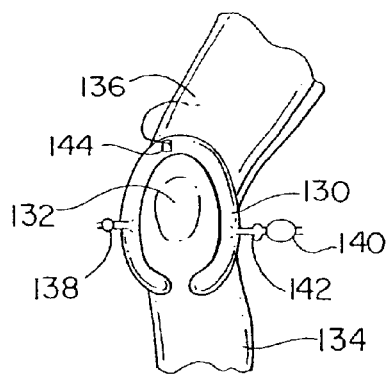
FIG. 3 is a perspective view of an alternative embodiment of a fluid bladder positioned by the knee of a patient without the remaining portions of the orthosis being present.

An alternative embodiment 130 of the bladder is depicted in FIG. 3 in position around a knee 132 without the rest of the brace present. The horse-shoe bladder 130 is similar to the toroidal bladder 114 except that a section of the toroid is removed. The horse-shoe bladder 130 can be positioned with the open portion oriented near the lower portion of the leg 134 or near the top portion of the leg 136. Horse-shoe bladder 130 is equipped with an outlet valve 138, a manual inflator 140 connected by way of a one-way valve 142 and a pressure sensor 144.

Figure 4:
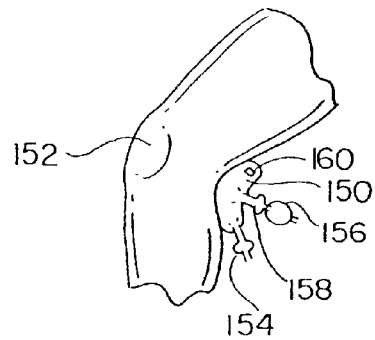
FIG. 4 is a side view of another alternative embodiment of the bladder positioned by the knee of a patient without the remaining portions of the orthosis being present.

Another alternative embodiment 150 of the bladder is depicted in FIG. 4. This roughly ellipsoidal bladder 150 is designed to be placed at the underside of the knee 152. It is also equipped with an outlet valve 154, a manual inflator 156 attached by way of a one-way valve 158 and a pressure sensor 160.

Figure 5:
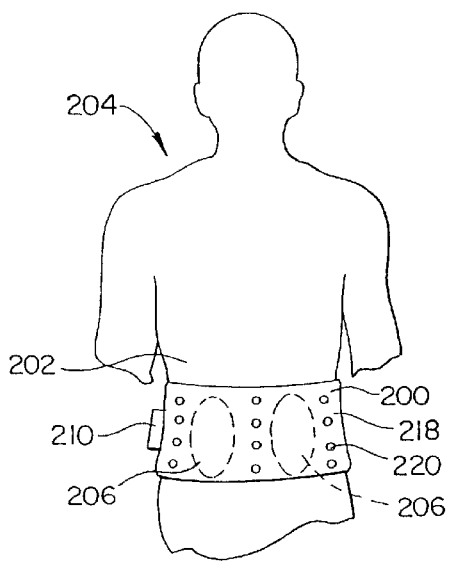
FIG. 5 is a perspective view of an exercise orthosis depicted around the lower back of a patient with fluid bladders under the surface outlined with dashed lines.

Referring to FIG. 5, an exercise orthosis 200 can be designed to fit the torso 202 of patient 204 in order to assist with back exercises. Back orthosis 200 can include one or more bladders 206. Preferably, a plurality of bladders 206 are included within back orthosis 200 to avoid putting pressure on the spine.

Back orthosis 200 should be positioned to support a portion of the back for exercise. A different orthosis may be needed to exercise each different portion of the back depending on the design of the orthoses. The brace can be used for isometric exercises or other exercises, such as scoliosis exercises where the patient moves counter to the forces being exerted on the back to decrease the forces.

Figure 6:
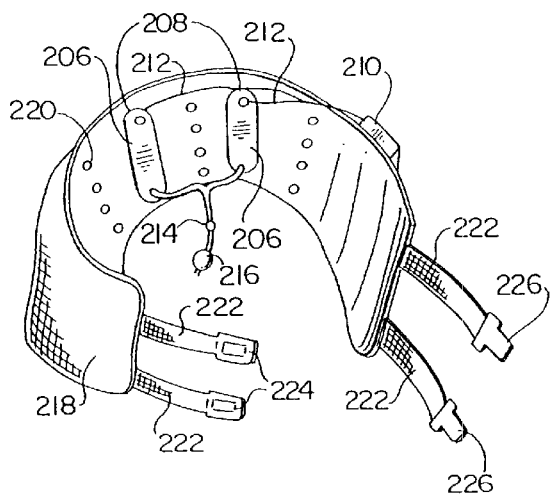
FIG. 6 is a perspective view of the exercise orthosis of FIG. 5 shown separately from the patient.

Referring to FIG. 6, at least one of bladders 206 includes a pressure sensor 208 to measure the pressure within the bladder 206. Pressure sensor 208 is attached to controller 210 by wire 212. Controller 210 functions similarly to controller 112 described with respect to FIG. 1. Bladders 206 can be filled and emptied in a variety of ways depending on the fluid used. In one preferred embodiment where air is the fluid, valve 214 is used to inflate or deflate both bladders 206 depicted. Detachable ball 216 can be used to inflate bladders 206 by manual pumping. Pressure generally is affected by the physical conditions such as temperature and positioning on the brace.

Referring to FIGS. 5 and 6, orthosis 200 preferably has a relatively rigid frame 218. Preferred materials for the frame include a variety of polymer materials, possibly combined with natural or synthetic fabric and/or metal. Ventilation holes 220 can be put in the frame 218. Padding can be included, if desired. A large variety of approaches can be used to secure the orthosis to the patient. FIG. 6 depicts a design using straps 222 having mated plastic clips 224, 226 attached to the ends of the straps 222. The exact number of straps and types of clips can be varied, as desired.

When the portion of the back within the orthosis is stressed, the pressure in bladders 206 will increase due to the forces exerted against the orthosis. As with the other embodiments of the exercise orthosis, the pressure fluctuations within the bladder reflect the forces exerted by the patient. Therefore, these pressure changes can be used to design a desirable exercise routine and monitor the patient's compliance with the target exercise routine.

Any of the exercise braces described above further can include an accelerometer. For example, in FIG. 1 accelerometer 160 is depicted on the orthosis 100. Appropriate accelerometers include, for example, single chip accelerometers described in the 1996 Allied Electronics Catalog. The accelerometer 160 can be used to monitor motions at other joints associated with the joint restrained by the brace. For example, an accelerometer 160 connected to the knee brace 100 can be used to measure motion at the hip joint. The accelerometer 160 preferably is connected to controller 112 for monitoring the accelerometer measurements. Measurements from the accelerometer 160 can be used to measure performance attributes of the patient, especially for athletically active or impaired patients.

The accelerometer can be especially useful with respect to a back orthosis. There are many ways of bending the back using a variety of muscles. In addition, there are methods of moving the back as a unit involving muscles outside of the back, e.g., hip muscles. The forces exerted by some of these muscles can be measured through the use of a strain gauge or a pressure gauge combined with the bladder embodiments as described above. Forces exerted by muscles connected to joints not within the brace cannot be measured by force measurements within the brace. Rapid accelerations of the body or spine may imply improper use or injury-prone behavior. The patient may be overcompensating through the use of other muscles for moving the back.

The use of an accelerometer can determine if the back is being moved generally. The measurements of the accelerometer provide an indication if these other muscles are being over-exerted by the patient. If desired, an alarm can be set up to respond if excessive acceleration is measured.

For use, the exercise orthosis is positioned around the intended portion of the body connecting two flexibly connected body portions. The orientation of the flexibly connected body portions is adjusted as necessary, for example, by adjusting hinges within the orthosis. The pressures within the bladders are adjusted to a appropriate rest pressure by changing the quantity of material within the bladder and/or by adjusting the relative position of the frame and bladder using straps or other adjustments. Once appropriately adjusted the patient exercises according to instructions provided by a health professional. A particular exercise routine may involve several orientations of the flexible body portions.

Preferably, the patient exercises according to an exercise routine designed by a physician based on the physical attributes of the patient. The controller provides feedback to the patient with respect to the actual performance relative to the target routine. In preferred embodiments, the controller keeps track of the patient's performance for evaluation by a health professional. The health professional can adjust the target exercise routine based on the recorded performance. The target performance can be made easier if the initial routine was too difficult or more difficult to account for progress in treatment. The exercise orthosis and the corrective back orthosis described below also can be used for behavior modification in terms of training an individual to use proper posture and the like.

Corrective Back Orthosis

As described above, bracing generally involves several challenges. The challenges for orthosis management are especially acute for scoliosis bracing. Here, with life threatening implications, the situation demands an optimum brace fit because the application of forces to the treated joints is indirect. The spine is simply not angled laterally, but it also may be rotated, many times in areas away from easily accessible contact points. Spinal curvature is complicated and aggravated by the dynamics of gravity, contracture and growth.

After leaving a fitting session, a brace may rapidly become loose, for example, due to weight loss or other fluctuation such as water-weight variation. The forces within the brace may deteriorate due to motor or viscoelastic responses as the brace is worn. In addition, the brace may be too tight such that compliance by the patient is difficult or impossible.

Furthermore, the efficient application of mechanical forces to complex curves of the spine, within the limits of soft tissue and bone anatomy, should be optimized by accurate quantitation of forces and their changing relationships, amplitudes and requirements over time. Single static adjustments of the brace are made by a physician or technician based on point of time information without information on the progression of events over time.

With respect to the present corrective orthosis, one or more of the force applicators that are used to apply desired corrective forces to the spine have corresponding sensors to measure the force being applied. The corrective forces are applied based on a determination of the corrective forces needed to arrest or reverse the misalignment. The applied forces generally can be applied to control longitudinal and other deformities such as pure anterior or posterior (kyphosis, lordosis), pure lateral bends (scoliosis) and combinations thereof (complex scoliosis).

The force measured by the sensors can be displayed for ease of adjustment. In alternative embodiments, one or more bladders are used as force applicators in a corrective back orthosis to provide cushioning of the forces. Monitoring the pressure in the fluid bladder provides a quantitative measurement related to the corrective forces.

The force measurements assist a person fitting the brace to set the forces at desirable levels. Also, the force measurements permit the patient to adjust the forces to appropriate values if changes in fit of the orthosis occur between visits to the attending health professional. If it is undesirable for patients to adjust the forces themselves, at least the patients can monitor for changes in the measured forces so that they can seek appropriate adjustment by professionals.

Preferably, the force sensors are connected to a microprocessor, which provides the capability to monitor the variation in applied corrective force over time. The monitored forces provided by the microprocessor assist invaluably with the assessment of the progress with the brace. Minimally, the microprocessor can be used to evaluate compliance by the patient, which is a major issue with scoliosis bracing. The brace cannot help if is not being worn. In addition, the force sensor can attach to an alarm either through the microprocessor or separately to provide a warning to the patient if the forces become excessive.

Furthermore, the microprocessor can assist with fitting the brace by providing a graphic display of the forces as they are adjusted. In an active adjustment mode, the microprocessor can alter the forces within the brace to ensure proper levels of force to correct for unexpected changes in the forces or to alter the forces as a function of time in response to expected changes in spinal curvature. For example, if fluid bladders are used, the amount of fluid within the bladder can be changed to adjust the force. Alternatively, strap or other adjustments can be made to alter the pressure without a pump.

Appropriate braces for these corrective orthoses support at least a significant portion of the patient's torso. The material used to make the brace should be relatively rigid, although some parts of the side portions can be flexible without diminishing the support significantly. Therefore, the patient's back is well supported and the forces applied by the orthosis are relatively constant. The brace can optionally include padding, which helps distribute the weight of the brace and thereby provides greater comfort.

Strain gauges can be attached to the frame to measure stresses within the frame. Changes in the applied forces generally occur along with changes in the fit of the frame on the patient. Changes in the fit of the frame results in corresponding changes in the stresses on the frame. Therefore, changes in stress can be used as another indicator of changes in corrective forces being applied. The strain gauges should be positioned at appropriate points along the frame to provide an indication of changes in orientation of the frame on the patient. These stress sensors may also provide a measure of the amount of force applied by the force applicators.

The stress sensors preferably are monitored by the microprocessor along with the force sensors. If the applied forces change sufficiently as measured by the force sensors and/or the strain gauges to indicate excess, misdirected or inadequate corrective forces, a warning can be provided that the forces need adjustment. Note that the force sensors and the strain gauges can both operate on similar or identical principle, but they are applied to different types of measurements.

In a preferred orthosis, the force applicators are repositionable so that they can be placed where desired and moved as treatment progresses, if appropriate. The locations of the force applicators can be programmed into the control unit. Based on the force measurements, the microprocessor preferably determines the force vectors and torques applied to the spine. These can be graphically displayed on the control unit to allow for adjustments to the forces. Then, these forces are monitored by the control unit during use to evaluate forces applied over time to the spine and to ensure compliance by the patient.

The microprocessor also can be programmed with the curvature of the spine. Then, the microprocessor can use a three dimensional polar view to account for twist in the spine as well as bends. The forces can be related to the orientation of the spine to assist the physician in setting the correct forces. The spinal curvature can be updated and reentered into the microprocessor at subsequent clinic visits.

Figure 7:
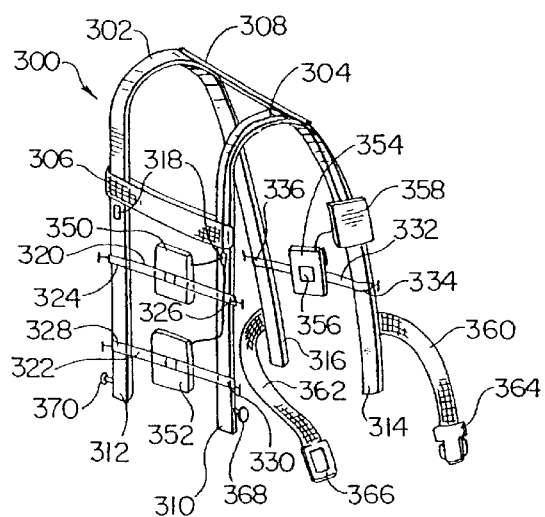
FIG. 7 is a perspective view of a corrective back orthosis of the invention.

Referring to FIG. 7, one embodiment of a corrective back orthosis 300 is displayed. Shoulder straps 302, 304 are connected to frame supports 306 and 308. Frame support 306 supports frame members 310 and 312. Frame support 308 supports frame members 314 and 316. Strain gauges 318 are located on frame members 310 and 312. Similar strain gauges can be placed on frame members 314 and 316 and/or frame supports 306 and 308.

Bars 320 and 322 are attached to frame members 310 and 312 with pairs of adjustable brackets 324, 326 and 328, 330, respectively. By loosening a pair of adjustable brackets, either 324 and 326 or 328 and 330, bars 320 and 322 can be moved up or down along frame members 310 and 312. Similarly, bar 332 is attached to frame members 314 and 316 at adjustable brackets 334 and 336. Loosening of adjustable brackets 334 and 336 permits the repositioning of bar 332 to a desired position where the adjustable brackets 334 and 336 are retightened.

Force applicators 350, 352 and 354 are located on bars 320, 322 and 332, respectively. Force applicators 350, 352 and 354 generally have a padded surface for contacting the patient. Force applicators preferably include a force sensor, such as pressure sensor 356, located on the padded surface or just below the padded surface. Pressure sensor 356 measure the forces applied to the patient as well as the pressure on the patient's skin. The pressure sensors can be of the types described above with respect to measuring pressure in a bladder. The pressure sensors preferably are connected to a control unit 358.

In alternative embodiments, the force applicators include fluid bladders with pressure sensors. The fluid bladders can be sealed with a fixed amount of fluid, or they can be designed for inflation and deflation.

The corrective back orthosis can include straps 360 and 362 attached to frame members 314 and 316. Straps 360 and 362 include buckles 364 and 366. Buckles 364 and 366 can be attached to knobs 368 and 370 to secure the orthosis on the patient. Alternatively, the straps can be attached to frame members 310 and 312. A variety of other fastening devices can be used to secure the orthosis.

Figure 8:
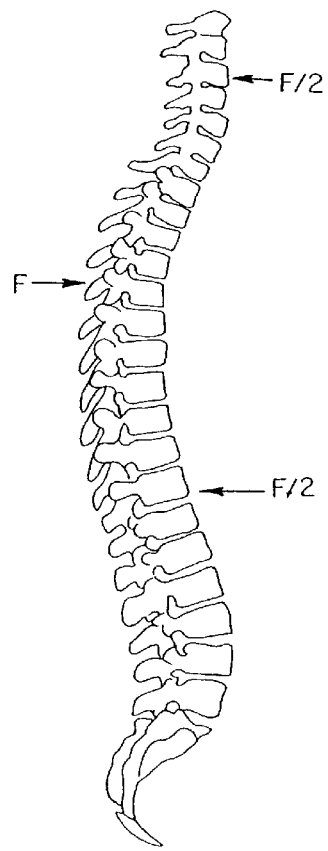
FIG. 8 is a schematic view of the forces applied to the spine at three points by the corrective back orthosis shown in FIG. 7.

The orthosis 300 is positioned on a patient to produce one, two, three or more points of force, as depicted in FIG. 8 with two points of force applied from the back and one point of force applied from the front. The bars are positioned to apply the forces at the desired height. The orthosis can be altered to include more than three force applicators such that forces are applied at more than three points. Similarly, the relative numbers of forces applied from the front and back can be changed.

Figure 9:
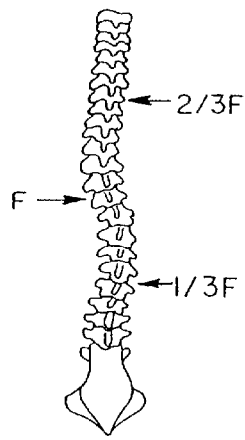
FIG. 9 is a schematic view of lateral forces applied by a corrective back orthosis.

The forces applied by corrective back orthosis 300 are directed in a front-to-back and back-to-front direction (collectively referred to as front-to-back forces below). Alternatively, forces can be applied with forces in a lateral direction as depicted in FIG. 9. Corrective back orthosis 400 in FIG. 10 provides for lateral components to the forces.

Figure 10:
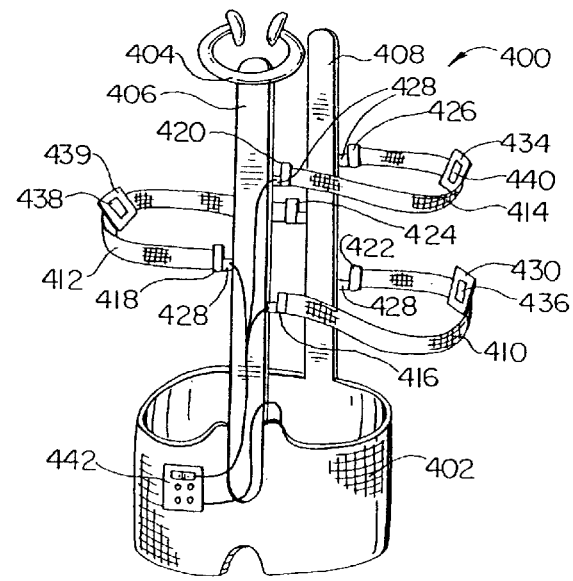
FIG. 10 is a perspective view of a corrective back orthosis of the invention that applies lateral forces to the spine of a patient.

FIG. 10 depicts an alternative embodiment 400 of the corrective back orthosis. Corrective back orthosis 400 has a pelvic girdle 402 and throat molds 404 connected by two upright supports 406 and 408. Upright support 406 is located along the front of the patient during use, and upright support 408 is located along the person's back. Corrective back orthosis 400 includes three side straps 410, 412 and 414. A different number of side straps can be used as desired.

Side straps 410, 412 and 414 are attached to the front upright support 406 at brackets 416, 418 and 420. Side straps 410, 412 and 414 are attached to the back upright support 408 at brackets 422, 424 and 426. Brackets 416–426 preferably are adjustable such that the position along the upright supports 406 and 408 can be set as desired. Brackets 416–426 preferably include strain gauges 428. Side straps 410, 412 and 414 can be detached in a variety of ways so that the orthosis 400 can be put on and taken off.

Side straps 410, 412 and 414 include force applicators 430, 432 and 434. Force applicators 430, 432 and 434 preferably include pressure sensors 436, 438 and 440. Pressure sensors 436, 438 and 440 can be connected to a control unit 442. Strain gauges 428 preferably are attached to control unit 442. Control unit 442 preferably includes a microprocessor as in other control units described above.

In alternative embodiments, the forces are supplied by one or more bladders, either alone or in combination with other types of force applicators. One or more of the bladders can include a pressure sensor. The pressure sensor can be used to monitor the forces against the skin as well as to monitor the corrective forces applied by the bladder. Appropriate pressure transducers have been described above with respect to exercise orthoses.

Corrective back orthoses 300 and 400 depicted in FIGS. 7 and 10, respectively, have a similar overall design. In preferred embodiments, the features can be combined to include force applicators positioned along the front and back as well as the sides. Other basic designs can be used to construct corrective back orthoses of the invention. One alternative design is depicted in FIGS. 11 and 12.

Figure 11:
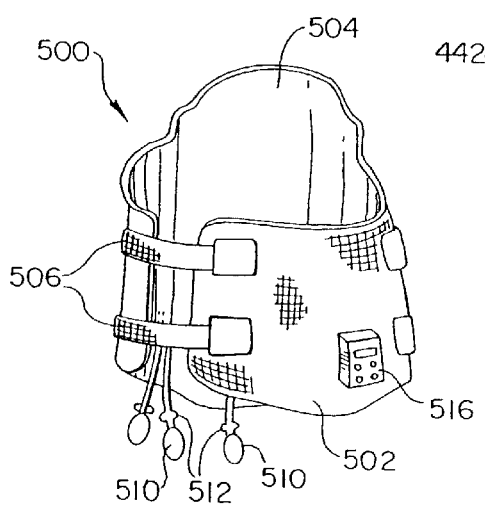
FIG. 11 is a perspective view of an alternative embodiment of a corrective back orthosis.
Figure 12:
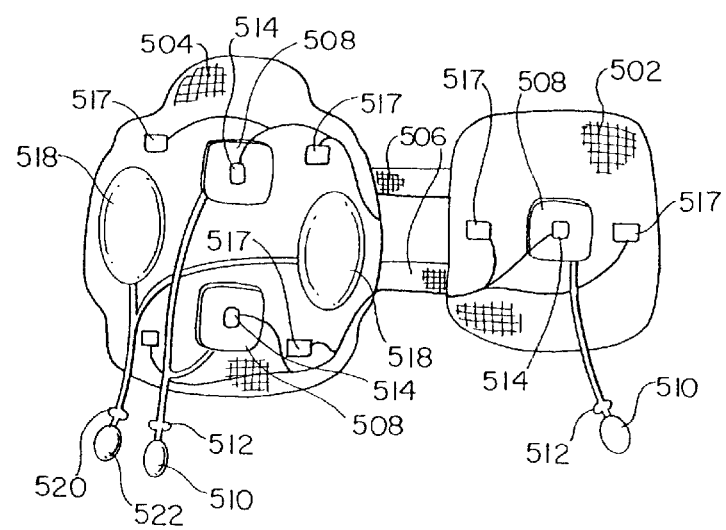
FIG. 12 is a front view of the corrective back orthosis of FIG. 11, where the orthosis is opened to display the structure within.

Referring to FIGS. 11 and 12, corrective back orthosis 500 includes a front support 502 and a back support 504. Front support 502 is connected to back support 504 by a series of straps 506 that can be disengaged to permit the patient to remove the orthosis 500. Force applicators 508 can be placed in appropriate positions within supports 502 and 504 such that desired levels of corrective forces are applied when the orthosis 500 is in place. Alternatively, the supports can be oriented along the patient's sides.

Removable bulbs 510 are used to pump air into bladders 508. Valves 512 control air flow into and out of bladders 508. Alternatively, electrical valves and pumps can be used to control the fluid in the bladders 508. Also, force applicators 508 can be pads or fluid bladders using fluids other than air. Fluid bladders are preferred such that the amount of force can be adjusted with the orthosis 500 in place by varying the amount of fluid within the bladder.

Force applicators 508 can be made repositionable, for example, by using hook and loop fasteners. A large fraction of the inner surfaces of supports 502 and 504 can be covered with loop fabric, and the backs of force applicators can include hook type fasteners. If the force applicators 508 are repositionable, the force applicators can be positioned as desired for a particular patient at a particular point in time. The force applicators 508 can be positioned to apply front-to-back forces or a combination of front-to-back forces and lateral forces. In alternative orientations of the supports, the force applicators can be positioned to apply lateral forces alone. The number of force applicators 508 can be varied as desired.

Force applicators 508 preferably include force sensors 514. Preferred force sensors are pressure sensors. Force sensors are connected to control unit 516. Strain gauges 517 are attached to supports 502 and 504. Strain gauges 517 preferably are connected to control unit 516.

Additional cushions 518 can be included for comfort. Additional cushions 518 can be pads or fluid bladders. If additional cushions 518 are air bladders, a valve 520 and bulb 522 can be included to fill and empty additional cushions 518.

For use, an initial examination of the patient generally takes place at a medical facility. Measurements are made of deformity parameters as well as normative data on progression of curve shape and resolution patterns needed to design treatment. Information on the spinal curvature is reproduced from measurements taken from x-rays. This information can be directly input into the control unit for the brace. More preferably, this information is first input into a base station, a microprocessor used by a health professional to track patient's condition and progress. A corrective vector prescription is determined based on the measurements.

The information can then be downloaded from the base station to the control unit by a variety of protocols. The base station processor and control unit processor can be connected by RS 232 connection, by telephone modem or other similar connections. Alternatively, the processors can transfer information through radio frequencies using transmitters and receivers.

A representation of the deformed spine and the corrective force vectors can be graphically displayed by the base station and/or the control unit. The force applicators are positioned to correspond to the locations of the force vectors. The pressures can then be set to correspond to the magnitudes of the corrective force vectors. The control unit preferably monitors the pressure measurements to provide a warning of excess, misdirected and/or inadequate corrective forces. The corrective forces are established according to desired parameters.

The patient generally then wears the brace away from the care of the health care provider. The control unit monitors compliance and any variation in the forces within the brace. The patient further can perform exercises within the brace. These scoliosis exercises generally involve motions directed by the force applicators to further the corrective activity. To perform these exercises, the patient moves to decrease the exerted forces of the force applicators. This requires muscular force directed similarly to the forces exerted by the force applicators. These exercises can be monitored by the control unit and later downloaded to a base station for evaluation by a health professional.

Information monitored by the control unit can be periodically downloaded to the base station. This information can be transferred by a hard wire connection, transmission using a modem over phone lines or by transmission using electromagnetic radiation such as radio waves or infrared radiation. The downloaded information can be evaluated by a health care professional. This information can be used to reevaluate the selected corrective parameters. Also, this information can be used to evaluate changes in the applied forces.

In addition, periodic examinations can be made to remeasure the deformity parameters. The deformity parameters preferably is input into the base station and/or the control unit. The new deformity parameters are used to select a new corrective force vector prescription. This process is then repeated until sufficient progress has been made that the treatment can be terminated, or if insufficient progress is obtained such that alternatives to bracing are attempted.

Other embodiments of exercise orthoses and corrective back orthoses are within the claims.

What is claimed is:

1. An orthopedic device comprising:

(a) a frame that restrains a first flexibly connected body portion of an individual relative to a second flexibly connected body portion;

(b) a bladder held by said frame, where said bladder contacts at least one of said flexibly connected body portions when said frame is restraining said flexibly connected body portions;

(c) a pressure sensor attached to said bladder such that pressure within said bladder is measured as a pressure measurement;

(d) a digital computer microprocessor operably connected to said pressure sensor to receive said pressure measurements, where said microprocessor monitors variations in pressure, provides instructions on exercises, and evaluates performance of the exercises based on pressure measurements;

(e) nonvolatile storage connected to said microprocessor; and (f) a display connected to said microprocessor to display a value related to said pressure measurements and said instructions on exercises.

2. The orthopedic restraining device of claim 1, wherein said frame comprises a hinge.

3. The orthopedic restraining device of claim 1, further comprising a releasable fastener that connects said bladder to said frame, such that said bladder is positionable relative to said frame to adjust said pressure within said bladder.

4. The orthopedic restraining device of claim 1, wherein said first flexibly connected body portion of said individual and said second flexibly connected body portion are connected by a hinge joint or ball and socket joint.

5. The orthopedic restraining device of claim 1, wherein said first flexibly connected body portion of said individual and said second flexibly connected body portion are connected by at least one vertebra.

6. The orthopedic restraining device of claim 1, wherein said bladder holds air.

7. The orthopedic restraining device of claim 1, further comprising an accelerometer operably connected to said orthopedic device, wherein the accelerometer measures acceleration of said flexibly connected body portions.

8. The orthopedic device of claim 1 wherein said bladder has a manual control to adjust the amount of fluid within the bladder.

9. A corrective back orthosis comprising:
(a) a frame that fits around at least a portion of a patient's torso to surround a portion of said patient's spine;
(b) a bladder supported by said frame, where said bladder is positioned to provide and provides corrective forces to said spine of said patient;
(c) a pressure sensor attached to said bladder such that the output of said pressure sensor varies according to the pressure within said bladder;
(d) a digital computer microprocessor operably connected to said pressure sensor and having an output interface connection for transferring information to another computer, wherein said microprocessor monitors variations in pressure; and
(e) nonvolatile storage connected to said microprocessor.

10. The corrective back orthosis of claim 8, further comprising a graphic display interfaced to said microprocessor, where said graphic display depicts the forces along spinal orientations of the patient.

11. The corrective back orthosis of claim 8, further comprising a valve in fluid communication with said bladder.

12. The corrective back orthosis of claim 8, further comprising an additional bladder supported by said frame.

13. A corrective back orthosis comprising:
(a) a frame that fits around at least a portion of a patient's torso to surround a portion of said patient's spine;
(b) a force applicator connected to said frame to apply force to said patient's spine, the force applicator supplying surfaces of connection for the transmission of directional forces between the frame and the patient, and wherein said force applicator is repositionable;
(c) a sensor operably connected to said force applicators such that readings from said sensor relate to forces associated with said force applicator;
(d) a control unit connected to said force sensor, wherein the control unit comprises a digital computer microprocessor that monitors forces measured by said sensor, said microprocessor having an output interface connection for transferring information to another computer; and
(e) nonvolatile storage connected to said microprocessor.

14. The corrective back orthosis of claim 13, further comprising a graphic display interfaced to said microprocessor, where said graphic display depicts forces along spinal orientations of said patient.

15. The corrective back orthosis of claim 13 wherein the force applicator comprises a bladder.

16. The corrective back orthosis of claim 13 wherein the frame comprises a strain gauge.

17. The corrective back orthosis of claim 13 further comprising an additional force applicator that is repositionable.

18. The corrective back orthosis of claim 17 wherein vectors of forces produced by the repositionable force applicators are represented by a graphic display.

* * * * *